United States Patent [19]

Strutt et al.

[11] 3,956,125
[45] May 11, 1976

[54] FILTRATION APPARATUS

[75] Inventors: Peter Strutt, Bramcote; Terrance Lymn, Glen Parva, both of England

[73] Assignee: Strutt & Farrands Ltd., Bramcote, England

[22] Filed: Aug. 12, 1974

[21] Appl. No.: 497,116

[30] Foreign Application Priority Data
Aug. 17, 1973 United Kingdom............... 38884/73

[52] U.S. Cl.................................. 210/94; 23/259; 23/292; 210/232; 210/239; 210/323 R; 210/406
[51] Int. Cl.²......................................... B01L 3/00
[58] Field of Search............... 23/259, 292; 210/94, 210/232, 238, 239, 240, 323, 340, 341, 406

[56] References Cited
UNITED STATES PATENTS

| | | | |
|---|---|---|---|
| 169,348 | 11/1875 | Fahlberg................................ | 23/259 |
| 2,190,220 | 2/1940 | Schilling................................ | 23/292 |
| 2,397,438 | 3/1946 | Schmid................................... | 23/292 X |
| 3,250,395 | 5/1966 | Blume..................................... | 23/292 X |
| 3,319,792 | 3/1967 | Leder et al. .......................... | 210/323 X |

OTHER PUBLICATIONS

Millipore Data Manual, Copyright 1963, p. 67.
Hackh's Chem. Dictionary, p. 298.
Millipore Catalog, MF 67, Copyright 1966, pp. 6, 33.

*Primary Examiner*—Charles N. Hart
*Assistant Examiner*—Robert G. Mukai
*Attorney, Agent, or Firm*—Larson, Taylor & Hinds

[57] ABSTRACT

Filtration apparatus is provided which enables a plurality of liquids to be filtered simultaneously. The apparatus basically comprises a tube adapted to be secured to a source of negative pressure, the tube having a plurality of upstanding inlets, each of which is adapted to receive a filtration paper holder. Liquid storage cylinders are adapted for mounting on the upper ends of the filtration paper holders so that liquid contained therein may be withdrawn through the filtration papers and into the tube. At least one filtrate collector is provided for optional removable mounting between at least one of the upstanding inlets and an associated filtration paper holder to collect a predetermined volume of the filtrate before the remainder of the filtrate passes down into the tube.

3 Claims, 1 Drawing Figure

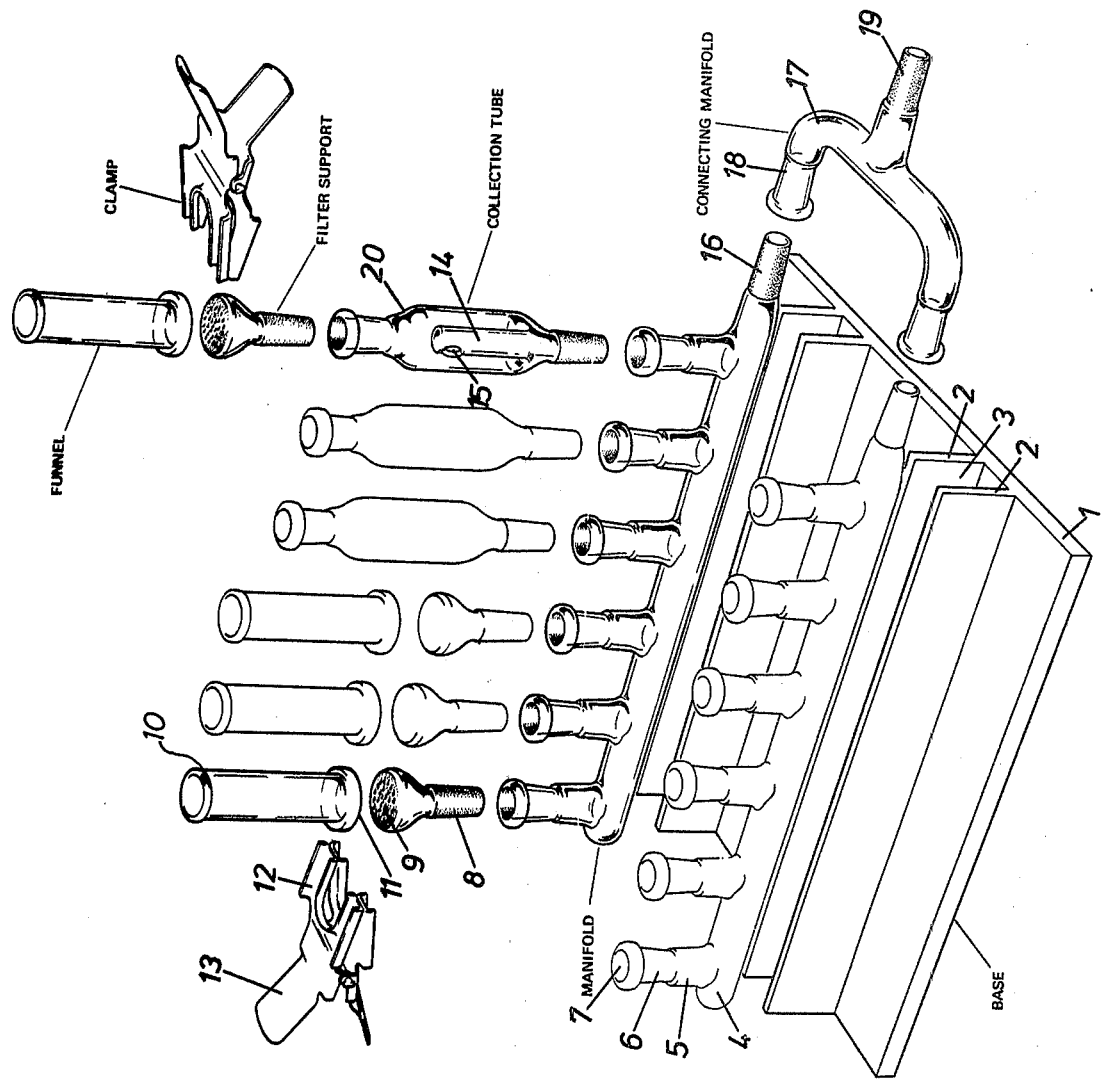

FILTRATION APPARATUS

This invention is for improvements in or relating to filtration apparatus and has for one object to provide improved apparatus for filtering of a plurality of liquids each containing different samples, whereafter it is desired to investigate the matter remaining upon the filter paper.

For example, it may be desirable to investigate by the use of radio-active isotopes, the functioning of certain parts of a human body and it is convenient to use a technique involving feeding to the human body at selected portions, radio-active isotopes and then taking samples from certain parts of the human body and by appropriate means fitering solutions to ascertain which parts of the body have traces of the isotopes.

Other uses for multi-filtration apparatus are well known. Hitherto, it has been the practice to provide a container, a holder for a multiplicity of filtration papers, and a liquid container consisting of a plurality of separate liquid containing devices which may be brought into register with the multiplicity of filtration papers. All three components are then clamped together and a vacuum applied to the container to draw the liquid through the filtration papers into the said container.

Numerous disadvantages occur with the apparatus of the aforementioned kind, and it is one object of the invention to provide a modified and improved form of multi-filtration apparatus.

According to the present invention there is provided a tube adapted to be secured to a source of negative pressure, the said tube having a plurality of upstanding inlets, each of which is adapted to receive a filtration paper holder, and means for locating a filtration paper holder relative to said inlets and for locating means for storing a liquid relative to said filtration paper holder above said paper holder so that liquid contained therein may be withdrawn through the filtration paper and into the aforementioned tube.

Desirably, the inlets to the tube are in the form of female ground glass apertures. The filtration paper holders each consist of a ground glass male member for location within the apertures and provided with means for locating a filtration paper relative thereto.

Temporarily secured above the filtration paper holder is a cylinder, preferably with a ground glass lower portion forming a liquid tight seal relative to the filtration paper, into which cylinder the liquid is poured. All the components may desirably be formed of borosilicate glass which is impervious to substantially all types of acids and alkalis used in filtration matters, particularly TCA (Trichloracetic acid).

If desired, a sample of the liquid which is the filtrate may be collected according to the present invention, and for this purpose the filter paper holder is replaced by an intermediate member consisting of a cylinder having an upstanding portion extending therein with an aperture of such location that a portion of liquid is firstly contained within the cylinder before it overflows through the aperture. The filtration paper holder may then be secured to one end of said intermediate member, while the other end of said intermediate member is secured into the inlet for said tube. All said joints are conveniently of ground glass standard sizes.

According to the present invention a plurality of tubes each connected to a plurality of filtration paper holders may simultaneously be connected to a source of negative pressure by a common manifold.

In order that the present invention may be more readily understood reference is now made to the drawing which illustrates in perspective an exploded form of the component parts of the apparatus forming the present invention.

There is provided a base with a pair of upstanding walls 2 which define a recess 3. The base and the walls 2 may be of any convenient material, such as for example solid acrylic plastics. The space 3 is provided for locating in substantially upright manner a tube of borosilicate glass provided with a plurality of portions 5, each of which is connected with a standard size female ground glass aperture 6 defining an inlet aperture 7, into which the plug or male portion 8 of a filtration paper holder 9 may be located. A cylinder 10 having a ground glass rim 11 is adapted to be secured above the filtration paper holder 9 by means of a clamp, consisting of a pair of spring urged flanges 12 which may be separated by hand operation of the wedges 13.

The cylinder 10 as illustrated is parallel sided. In some installations height may be at a premium in which event it is convenient for the cylinder 10 to be angled at approximately 45° to the vertical. It will be appreciated that the angled portion is integral with ground glass rim 11.

The tube 4 is provided with a ground glass male outlet member 16 which is adapted to be engaged with a source of negative pressure, and as illustrated in the present drawings a pair of tubes 4 are adapted to be secured to a common manifold 17. The ground glass male portion 16 engages into ground glass female portion 18 of the common manifold 17, and the common manifold 17 has a common ground glass outlet 19 for connecting to a source of negative pressure.

In an alternative illustrated in the righthand side of the accompanying drawing, the filtration member 9 is replace by a sampling bottle consisting of a cylinder 20, provided with an upstanding hollow portion 14 terminating in the outlet 15, so that as the filtrate is drawn through the filtration member 9 into the cylinder 20 the liquid is first retained in the cylinder 20 until it reaches up the stem of the spigot 14 and is then able to overflow into the tube wall through the aperture 15.

In use it will be appreciated that a plurality of filtration members 9 are connected to their respective sockets 6 and filter papers placed on to the surfaces 9 and then the cylinders 10 clamped into position. The apparatus is then appropriately connected to a source of negative pressure and the solutions to be filtered are then poured respectively into the cylinders 10.

If only a limited number of solutions are to be filtered then any spare aperture 6 may be blanked off by a solid plug of a ground glass nature or by a cork or by other appropriate means not specifically illustrated in the accompanying drawing.

It will be appreciated that the present invention provides filtration apparatus which is both relatively simple to manufacture, particularly easy to disassemble for cleaning purposes and sterilizing purposes, and which is interchangable so that should any parts be broken other parts may be readily replaced, and which is simple to use and which provides for a variety of different functions, particularly the facility of collecting the filtrate solution in the sampling cylinder 20.

What we claim is:

1. Filtration apparatus comprising an elongate tube, means for connecting said tube to a source of negative pressure, said tube having a plurality of tubular inlet passages formed integrally therewith and upstanding therefrom in spaced relationship therealong, each inlet passage terminating at its outer end in a female aperature, a plurality of hollow filtration paper holders for removable mounting in said female apertures, each holder having a lower male member and an upper end of ground glass constructed and arranged to support a filtration paper thereon, a plurality of liquid storage cylinders each having a ground glass lower portion for removable mounting on the upper end of one of said holders to form a liquid seal relative to a filtration paper mounted on said upper end of said holder, so that liquid in one or more of said storage cylinders may be withdrawn through a filtration paper, through a paper holder, and thence into said tube, clamping means constructed and arranged to maintain said liquid seal, and at least one filtrate collector for optional removable mounting between at least one of said upstanding inlets and an associated filtration paper holder, each said filtrate collector comprising a glass member constructed and arranged to trap a predetermined volume of the filtrate liquid after passing through said filtration paper holder, and having a lower male member for engaging said female aperture of one of said inlet passages and an upper female member for receiving the lower male member of one of said filtration paper holders, and having between the lower male member and upper female member a reservoir with an upstanding pierced outlet whereby liquid first entering said reservoir is stored therein and only overflows into said pierced outlet when the volume in said reservoir has reached a predetermined value, whereby said apparatus can be quickly and easily assembled with appropriate components and disassembled and cleaned thereafter.

2. Apparatus as claimed in claim 1 wherein all connections between said tubular inlets, said filtration paper holders, said storage cylinders, and said at least one filtrate collector are of ground glass.

3. Apparatus as claimed in claim 2 in which the components are formed of borosilicate glass.

* * * * *